United States Patent [19]
Anderson

[11] Patent Number: 5,267,129
[45] Date of Patent: Nov. 30, 1993

[54] PNEUMATIC LIGHTING APPARATUS

[75] Inventor: Marty J. Anderson, California, Mo.

[73] Assignee: PNU-Light Tool Works, Inc., Springfield, Mo.

[21] Appl. No.: 919,530

[22] Filed: Jul. 24, 1992

[51] Int. Cl.$^5$ .............................................. F21L 13/02
[52] U.S. Cl. ...................... 362/96; 362/118; 362/192
[58] Field of Search ............... 362/119, 120, 192, 193, 362/96

[56] References Cited

U.S. PATENT DOCUMENTS

| | | | |
|---|---|---|---|
| 1,528,754 | 3/1925 | Bresson | 362/192 |
| 1,607,562 | 11/1926 | Potter | 362/192 |
| 1,695,794 | 12/1928 | Becker, Jr. | 362/192 |
| 2,525,588 | 10/1950 | Cameron et al. | |
| 3,590,232 | 6/1971 | Sadowski | |
| 3,614,414 | 4/1972 | Gores | |
| 3,728,027 | 4/1973 | Watanabe | |
| 3,845,291 | 10/1974 | Portyrata | 362/192 |
| 4,230,453 | 10/1980 | Reimers | |
| 4,564,889 | 1/1986 | Bolson | 362/192 |
| 4,616,298 | 10/1986 | Bolson | 362/192 |
| 4,835,410 | 5/1989 | Bhagwat et al. | |
| 4,973,205 | 11/1990 | Spaulding | |

*Primary Examiner*—Richard R. Cole
*Attorney, Agent, or Firm*—Hovey, Williams, Timmons & Collins

[57] ABSTRACT

A pneumatic lighting apparatus for use with a pneumatically driven tool includes a pneumatic motor driven by compressed air, and an electrical generator that is driven by the mechanical output of the motor for generating an electrical current. A lamp is provided in a circuit with the generator for emitting light adapted to be directed onto an area in which the tool is being used. A conduit is provided which is connected between the outlet of the motor and an inlet of the tool in order to deliver compressed air from the apparatus to the tool. In order to permit control of the lighting apparatus independent of operation of the tool, a control valve is provided for controlling the flow of compressed air through the motor, and an exhaust valve controls the flow of compressed air between the conduit and an exhaust.

26 Claims, 5 Drawing Sheets

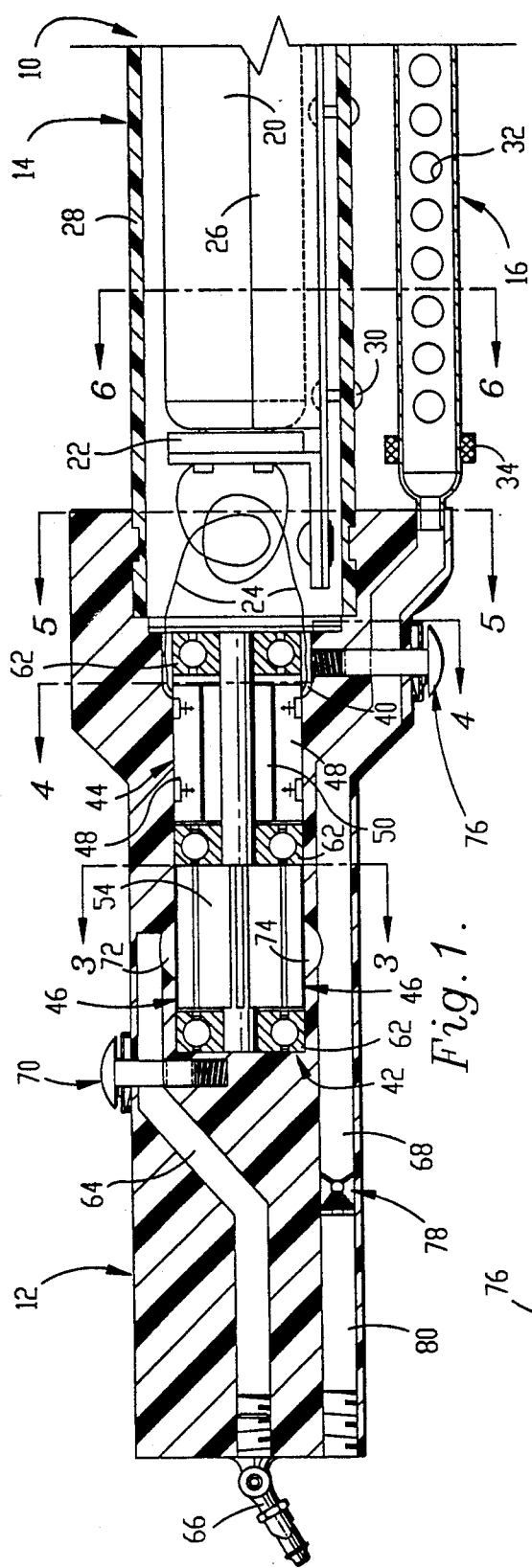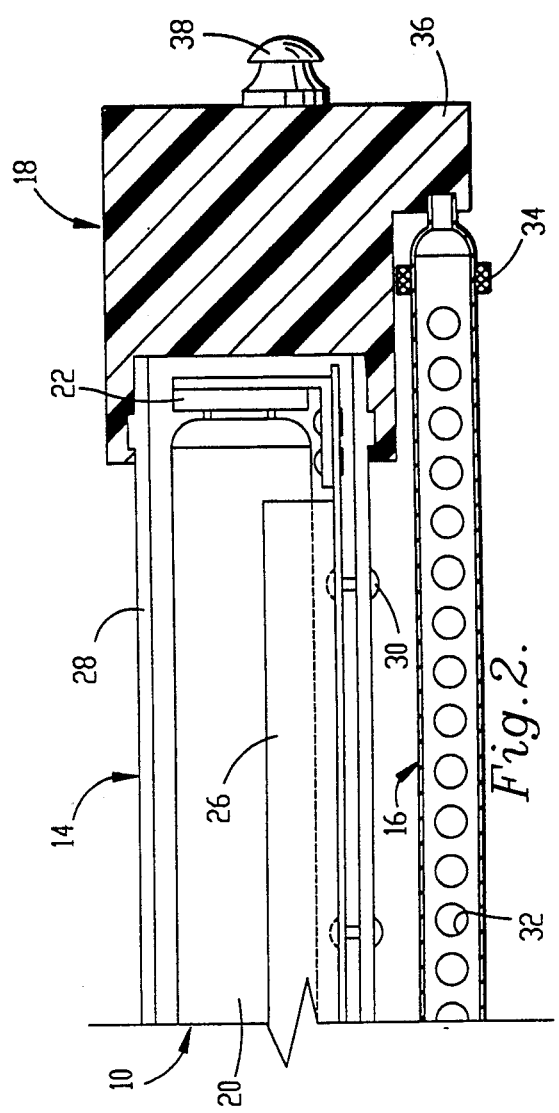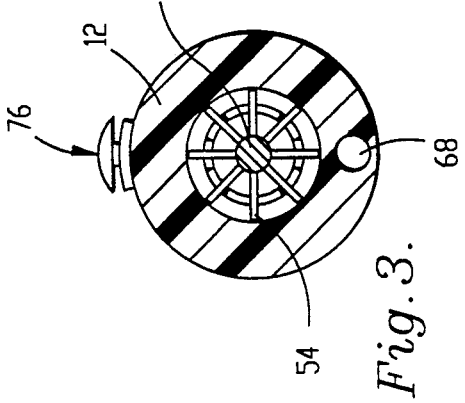

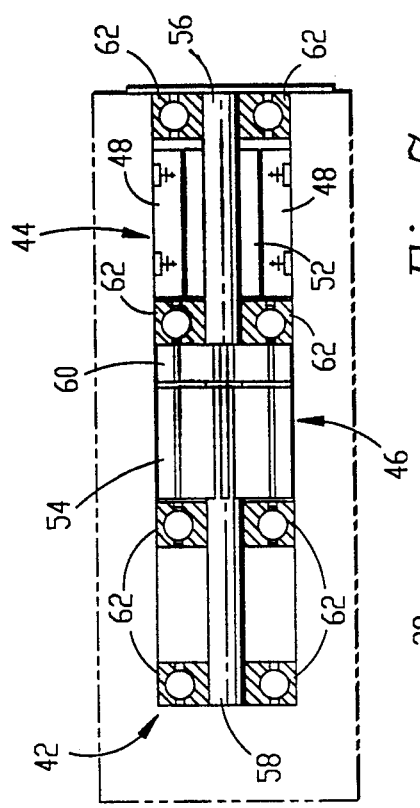
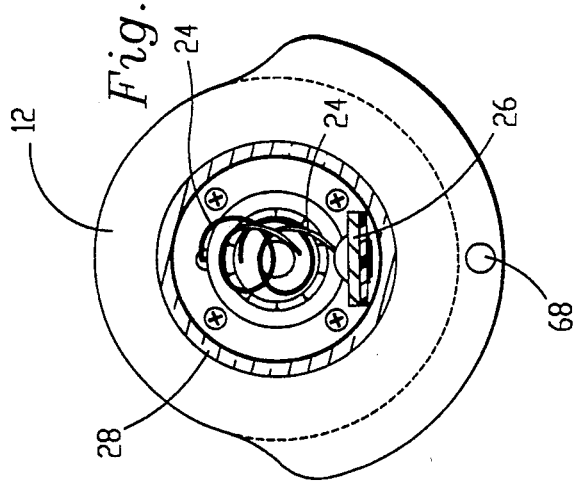
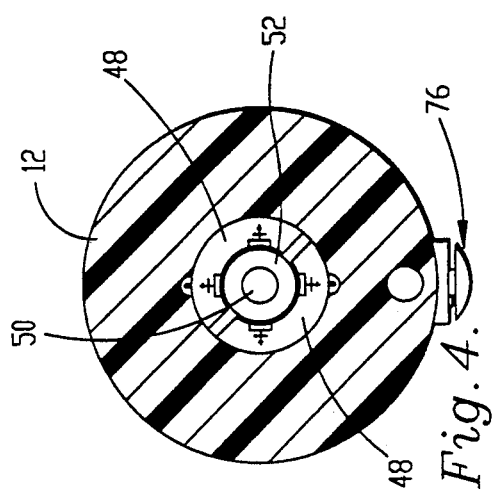

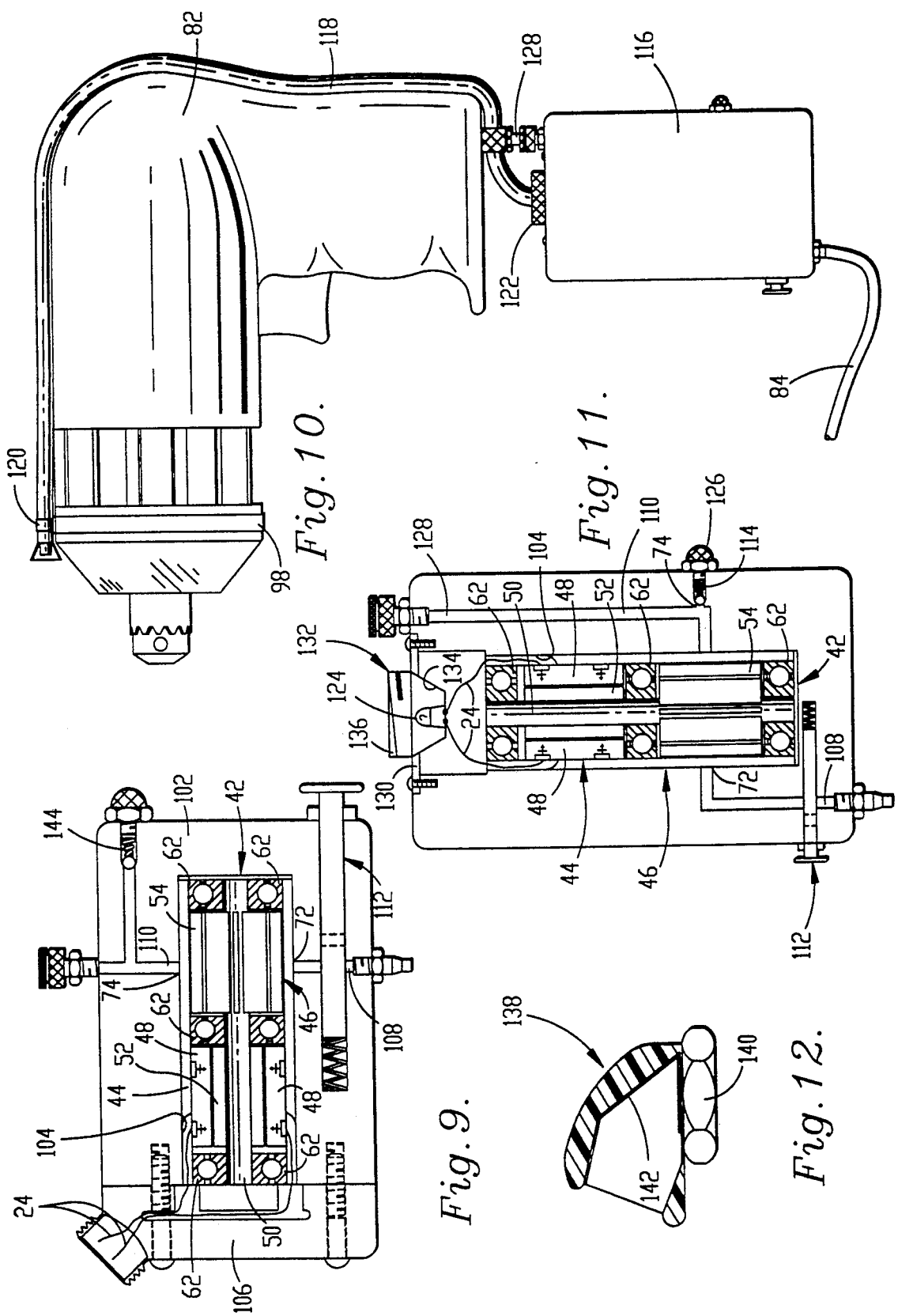

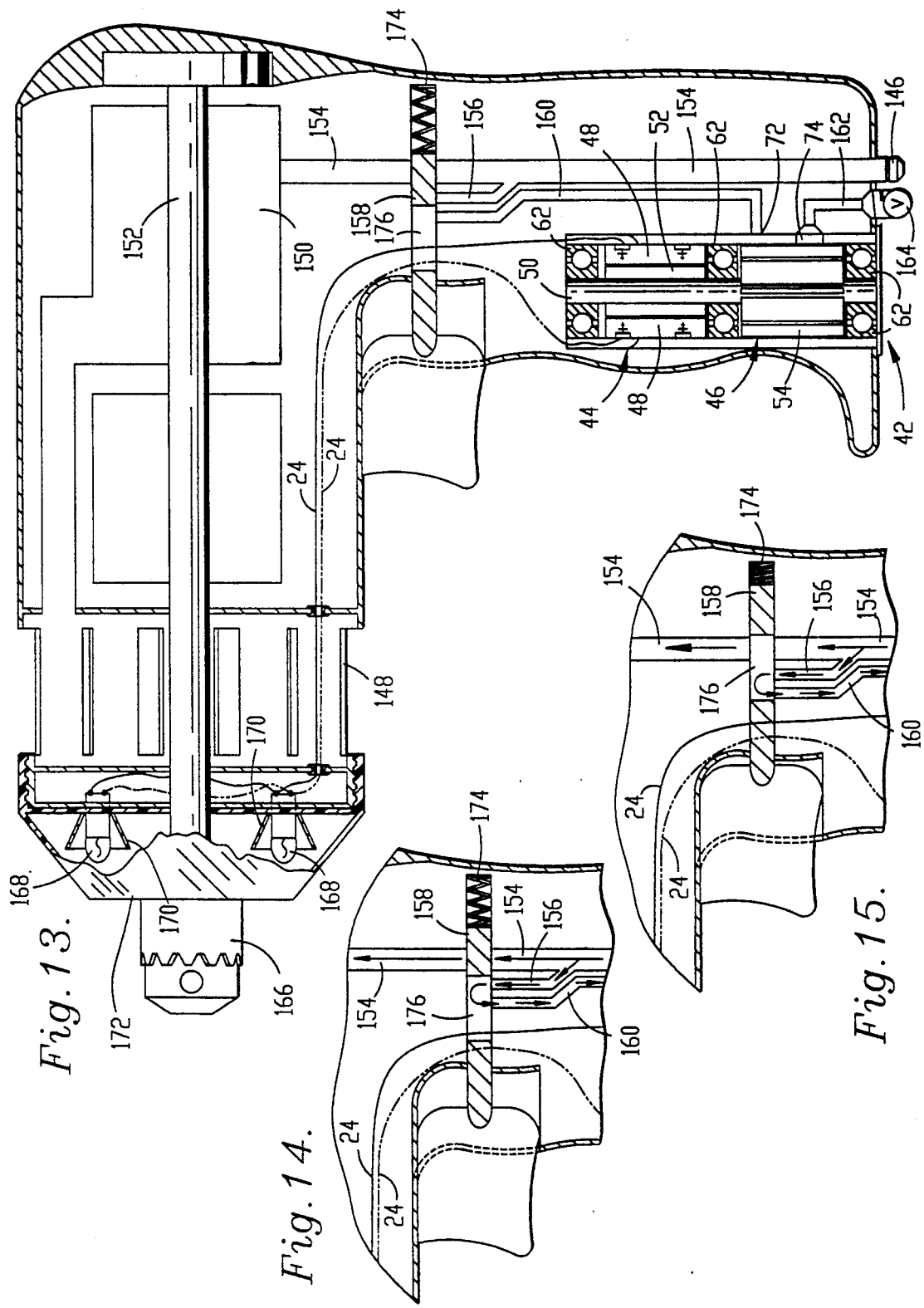

PNEUMATIC LIGHTING APPARATUS

BACKGROUND OF THE INVENTION

1. Field of the Invention

The present invention relates generally to lighting devices and, more particularly, to a pneumatic lighting apparatus for use with a pneumatic lighting apparatus for illuminating a work area in which the tool is to be used.

2. Discussion of the Prior Art

In many manufacturing and industrial maintenance setting, pneumatic tools are used to construct and repair products. In these settings, frequently a worker is required to access a small, hard to reach place that is out of the line of normal illumination of conventional manufacturing area lighting. It is common for the worker to carry a DC or AC powered, hand-held light in order to provide additional lighting of the immediate work area.

However, because conventional lighting devices typically must be hand-held, the worker may quickly become tied up between handling the tool and the light while also positioning himself and the work piece in a proper orientation. Further, because pneumatic power is already commonly available in the work place for use in powering the tools typically used, the provision of a separate DC or AC power source in addition to the pneumatic lines already present represents unnecessary duplication of power lines in the work area which inhibits movement of workers and reduces their efficiency.

Another disadvantage to using most presently available DC powered lighting devices is environmental in nature, and relates to the problem of disposal of batteries and the like which are used to supply the power for such devices. It would be desirable to provide a lighting apparatus that does not adversely effect the environment and that is powered by already available pneumatic means typically present in a manufacturing or maintenance environment.

OBJECTS AND SUMMARY OF THE INVENTION

It is an object of the present invention to provide a lighting apparatus which can be used in association with pneumatic tools in order to provide focused light onto the immediate area surrounding the point at which work is being done or at which a tool is directed, wherein the lighting apparatus is powered by the same pneumatic energy used to power the tools.

It is another object of the invention to provide a lighting apparatus that is pneumatically driven, and which includes ventilation means for selectively directing exhausted air from the apparatus into a desired region in which a worker is disposed.

Yet another object of the invention is to provide a pneumatic tool constructed with a light that is powered by compressed air and positioned to direct light onto the area in which work is being carried out by the tool.

These and other objects are evident from a review of the following description of a preferred embodiment of the invention, one aspect of which relates to a pneumatic lighting apparatus for use with a pneumatically driven tool.

According to this aspect of the invention, the lighting apparatus includes a lamp for emitting light adapted to be directed onto an area in which the tool is being used; a generator housing including an inlet adapted for connection to a source of compressed air, an outlet, and an exhaust; and a conduit for connecting the outlet of the housing with an air inlet of the tool to deliver compressed air from the apparatus to the tool. A pneumatic motor is disposed in the housing and is connected between the inlet and the outlet, the motor being driven by compressed air passing through the apparatus and providing a mechanical output. An electrical generator is driven by the mechanical output of the motor for generating electrical current, and an electrical circuit is provided which includes the generator and the lamp for supplying electricity to the lamp.

The apparatus further includes a control valve means for controlling the flow of compressed air through the motor, and an exhaust valve means for controlling the flow of compressed air from the exhaust, the exhaust valve means permitting compressed air to flow from the exhaust when the tool is not in use so that the lighting apparatus may be used independent of the tool.

Numerous advantageous results are achieved through the use of this construction. For example, by providing both an outlet from the apparatus to the tool, and an exhaust, and by employing an exhaust valve means, it is possible to permit operation of the lighting apparatus independent of operation of the tool so that the light may be operated even when the tool is not.

Further, because the lighting apparatus is driven by compressed air, the same lines extending between the source of compressed air and the tools may be used in driving the lighting apparatus, and additional power lines are not required. Also, because it is not necessary to use batteries in this construction of the invention, no adverse environmental impact occurs.

According to another aspect of the invention the lighting apparatus and power tool are formed in a single construction possessing many of the same advantages exhibited by the independent lighting apparatus.

According to yet another aspect of the invention a pneumatic lighting apparatus is provided which includes a ventilation means for exhausting compressed air from the apparatus after the compressed air has passed through the pneumatic motor, the ventilation means including means for changing the direction in which the air is exhausted relative to the apparatus. By providing such a construction, many of the advantages previously described are again achieved, and a worker is able to use exhausted air as a means for keeping cool while working in cramped, confined spaces.

BRIEF DESCRIPTION OF THE DRAWING FIGURES

A preferred embodiment of the present invention is described in detail below with reference to the attached drawing figures, wherein:

FIGS. 1 and 2 are a side sectional view of a pneumatic light constructed in accordance with a first preferred construction of the present invention;

FIG. 3 is a cross-sectional view taken along line 3—3 of FIG. 1, illustrating the construction of a pneumatic motor employed in the first preferred construction;

FIG. 4 is a cross-sectional view taken along line 4—4 of FIG. 1, illustrating the construction of an electrical generator employed in the first preferred construction;

FIG. 5 is a cross-sectional view taken along line 5—5 of FIG. 1, illustrating the construction of an end of the handle body of the pneumatic light of the first preferred construction;

FIG. 6 is a cross-sectional view taken along line 6—6 of FIG. 1, illustrating the construction of a lamp, reflector and lens employed in the first preferred construction, as well as a ventilation manifold;

FIG. 7 is a sectional view of a generator assembly having a modified construction;

FIG. 9 is a cross-sectional view of a generator housing of the lighting apparatus, illustrating a pneumatic motor and electrical generator employed in the second preferred construction;

FIG. 10 is a side elevational view of a pneumatic tool and a lighting apparatus constructed in accordance with a third preferred construction of the present invention;

FIG. 11 is a cross-sectional view of a generator housing of the lighting apparatus, illustrating a pneumatic motor and electrical generator employed in the third preferred construction;

FIG. 12 is a side sectional view of a rotatable lens socket adapted for use on the generator housing illustrated in FIG. 11;

FIG. 13 is a side sectional view of a pneumatic tool and a lighting apparatus constructed in accordance with a fourth preferred construction of the present invention;

FIG. 14 is a fragmentary view of a flow control valve employed in the tool of the fourth preferred construction, illustrating the valve in a partially actuated position;

FIG. 15 is a fragmentary view of a flow control valve employed in the tool of the fourth preferred construction, illustrating the valve in a fully actuated position.

DETAILED DESCRIPTION OF THE PREFERRED EMBODIMENT

Figure 16:
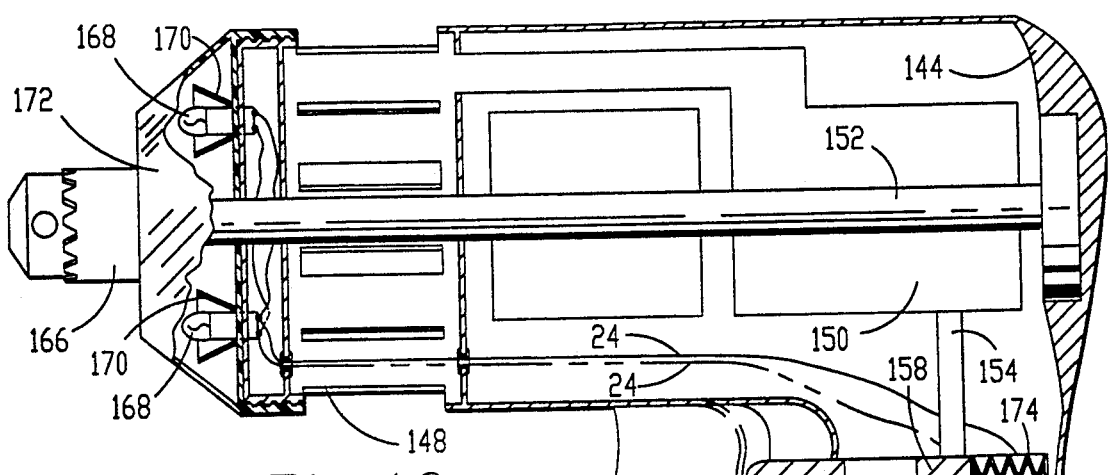
FIG. 16 is a side sectional view of a pneumatic tool and a lighting apparatus constructed in accordance with a fifth preferred construction of the present invention.

A pneumatic light constructed in accordance with a first preferred construction of the present invention is illustrated in FIGS. 1 and 2, which together show the entire apparatus. The light 10 includes a handle body 12, a lamp assembly 14, a ventilation manifold 16, and an end cap 18.

The lamp assembly 14 includes a lamp 20 of any suitable conventional construction, e.g. a 15-20W incandescent bulb, and is mounted in a pair of lamp sockets 22 adapted to receive and support the lamp and to connect the electrical contacts of the lamp with a pair of wires 24 extending between the lamp assembly and the handle body 12.

As shown in FIG. 6, the sockets 22 are supported on a reflector 26 formed of a sheet of material having a central section and a pair of lateral wings angled relative to the central section. The reflector 26 may be formed of plastic, e.g. nylon; metal; or any other suitable material capable of being formed with a reflective surface, and serves the purpose of directing light emitted from the lamp to one side of the apparatus.

The reflector 26, sockets 22 and lamp 20 are supported within a lens 28 which extends around the lamp and reflector along the length thereof. Preferably, plastic fasteners 30 or the like are used to secure the reflector to the lens. The lens 28 may also be formed of plastic, e.g. nylon, or any other clear material capable of focusing the light from the lamp while withstanding the environment within which the apparatus is to be employed. Where the apparatus is to be used in hazardous or otherwise extreme conditions, the lens may include a double enclosure, or may be formed with some other type of reinforcement for protecting the lens and lamp against breakage.

Returning to FIGS. 1 and 2, each end of the lens 28 is provided with a threaded or grooved outer circumferential surface adapted to mate with a cooperating surface provided on the handle body 12 and on the end cap 18. Once the lamp is fitted in the sockets and positioned within the lens, the lens is threaded into or otherwise secured between the handle body and end cap.

The ventilation manifold 16 is formed of aluminum or any other suitable material also extends between the handle body 12 and the end cap 18. The ventilation manifold is hollow and includes a plurality of openings 32 of any desired shape and size. At least one knurled ring 34 is affixed to the manifold to permit twisting of the manifold relative to the handle body in order to orient the holes in a desired direction relative to the apparatus.

As shown in FIG. 2, the end cap includes a depending portion 36 which retains the ventilation manifold between the cap and the handle body. In addition to providing this support to the manifold, the end cap 18 also adds rigidity to the overall apparatus. It is formed of plastic, e.g. nylon, or any other suitable material, and is provided with a button 28 at the remote or distal end thereof from which the apparatus may be suspended by a hook or the like which is not shown.

The handle body 12 is shown in FIG. 1, and is formed of a plastic, e.g. nylon, or other suitable material or combination of materials. A central cavity 40 is formed in the handle body and may be provided with a metal sleeve lining the cavity to provide any necessary construction tolerances. A drive assembly 42 is provided which is sized for receipt within the central cavity. The drive assembly 42 includes an electrical generator 44 and a pneumatic motor 46. The assembly 42 is preferably constructed as a unitary assembly that is fastened in the central cavity by a plurality of screws or the like, as shown in FIG. 5. The assembly 42 may be removed from the cavity, if desired, simply by removing the screws and pulling the unitary assembly from the cavity.

Turning to FIG. 4, the electrical generator 44 is shown to include a pair of stator coils 48 each formed of semi-cylindrical shape opposing one another relative to a rotor shaft 50 extending between the stator coils. The rotor shaft 50 supports an annular permanent magnet 52 for rotation therewith so that a current is generated in the coils 48 upon rotation of the rotor shaft and magnet. It is understood that any type of conventional rotor magnet may be used in the generator to obtain the desired output current. Further, although the generator illustrated produces AC current, DC generators are also known which may be used.

The pneumatic motor of the drive assembly is illustrated in FIG. 3, and includes an extension of the rotor shaft, and a plurality of blades or vanes affixed to the rotor shaft extension at one axial end thereof. Thus, the motor 46 is in the form of a turbine adapted to be rotated by compressed air in order to provide rotational input to the rotor shaft of the electrical generator 44.

Although the rotor shaft 50 also forms the shaft of the motor, it is understood that separate, collinear shafts 56, 58 may be provided, as shown in FIG. 7, in order to isolate the electrical generator from the motor. In this variation of the drive assembly, separate vanes 60 may be provided on the end of the rotor shaft adjacent the vanes 54 of the motor so that the air currents created during rotation of the axial shaft 58 of the motor induce rotation of the rotor shaft 56. Alternately, other constructions are also possible of the pneumatic motor. For example, it is possible to construct the motor with a shaft provided with ports in the circumferential surface thereof which catch compressed air delivered through the nozzle causing the shaft to rotate.

Returning again to FIG. 1, a sealed bearing assembly 62 is provided at each end of the shaft 50. An additional sealed bearing assembly 62 may be provided between the blades or vanes of the motor and the generator in order to seal the motor from the generator to prevent the escape of sparks from the generator and to increase the efficiency of the motor.

The handle body 12 includes an inlet passage 64 extending between a pivotal inlet connector 66 and the pneumatic motor 46, and an outlet passage 68 leading from the pneumatic motor. A valve 70 is provided in the inlet passage for controlling the flow of compressed air to the motor. The valve 70 is a conventional regulator valve capable of controlling the amount of compressed air delivered to the motor. The nozzle 72 opening up to the vanes of the motor from the inlet passage is preferably angled so that compressed air entering the motor drives the shaft 50. However, it is also possible to curve the vanes to facilitate rotation of the shaft 50 when compressed air is passed through the motor.

An outlet nozzle 74 permits communication between the motor 46 and the outlet passage 68, and a regulator valve 76 is disposed within the outlet passage for controlling the flow of compressed air from the motor to the ventilation manifold 16. The regulator valve 76 may be formed of any desired construction, but preferably allows an operator to control the amount of air delivered to the manifold in order to supply a desired amount of cooling air through the openings 32.

A check valve 78 is positioned between the nozzle and an exhaust 80 so that air is exhausted from the apparatus during operation when the ventilation manifold 16 is not in use. It is possible to employ a single valve in place of the valves 76, 78 in order to perform the same function while simplifying the construction of the apparatus.

Figure 8:
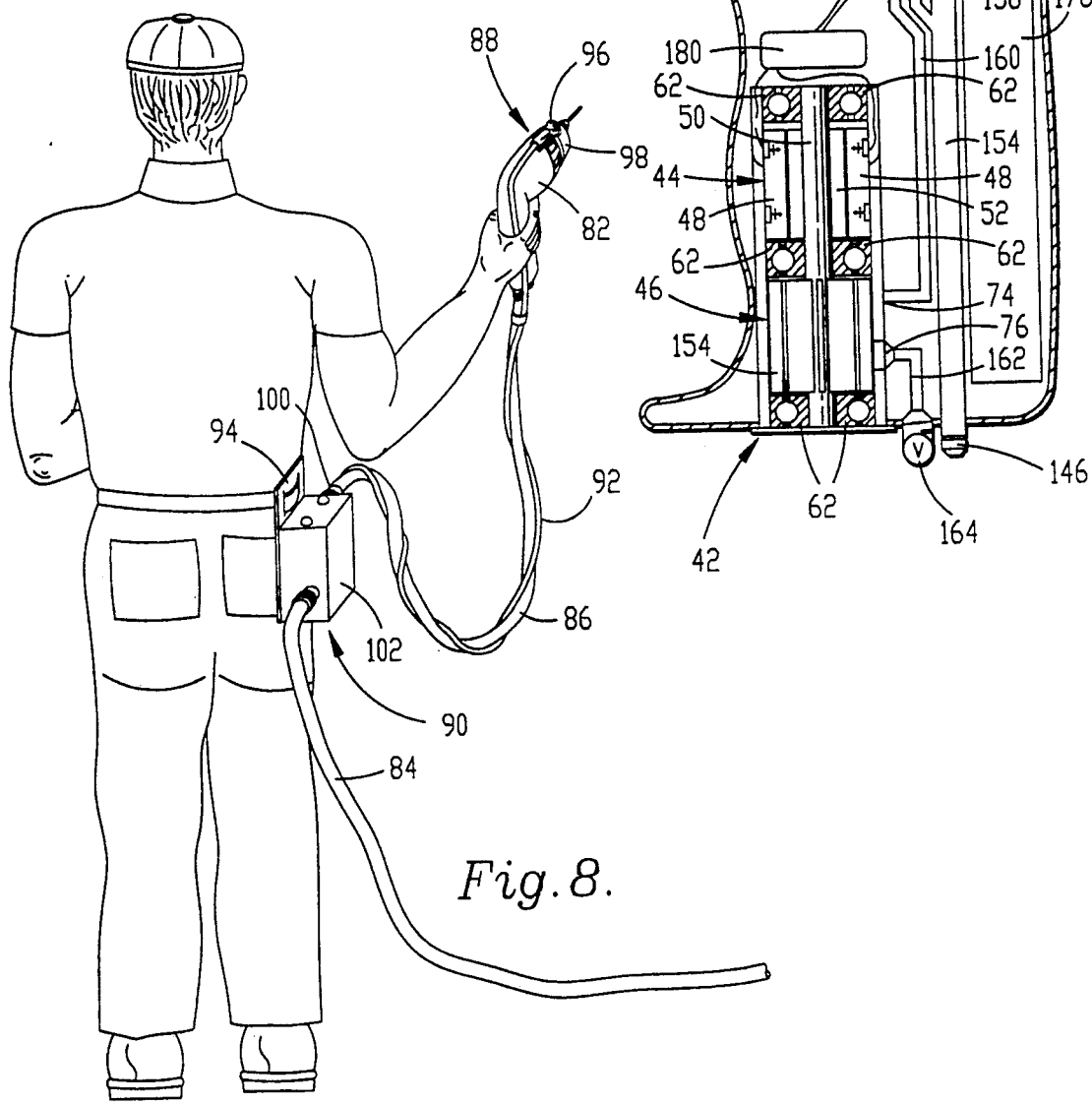
FIG. 8 is a perspective view of a user holding a pneumatic tool and a lighting apparatus constructed in accordance with a second preferred construction of the invention.

A pneumatic tool 82 and a lighting apparatus constructed in accordance with a second preferred construction of the invention is illustrated in FIG. 8. The tool is of conventional construction and may be any one of a number of types of tools which are pneumatically driven and which include an output shaft that is either rotated or oscillated along its axis in order to carry out a tool operation. The tool illustrated as a pneumatic drill.

When the tool is to be operated without the lighting apparatus, a supply line 84 of compressed air is coupled directly with the inlet of the tool to deliver compressed air to drive the tool. However, if it is desired to employ a lighting apparatus constructed in accordance with the second preferred construction of the invention, the supply line 84 is connected to the apparatus and an additional conduit or line 86 is provided between the lighting apparatus and the inlet of the tool.

The lighting apparatus includes a lamp assembly 88, a means for mounting the lamp assembly on the tool, a generator assembly 90, and an electrical power cord 92 extending between the lamp assembly and the generator assembly. In addition, a harness 94 may be provided for supporting the generator assembly from the belt of a user.

The lamp assembly 88 includes a conventional lamp secured within a socket which connects the contacts of the lamp with conductors provided in the electrical power cord. A reflector 96 surrounds the socket and functions to focus the light onto the immediate area surrounding the point at which work is being done or at which the tool is directed. A lens may also be provided on the assembly for further focusing or directing the light emitted by the lamp.

The mounting means preferably includes a removable strap 98 which fits around the tool body, and a clip secured to the strap for holding the light assembly in position. Although not shown clearly in FIG. 8, the mounting means is substantially the same as the strap and clip shown in the construction of FIG. 10, described below.

Returning to FIG. 8, the power cord 92 includes a pair of conductors extending within a protective covering of rubber of the like, and a coupling 100 is provided for connecting the cord with the generator assembly 90.

As shown in FIG. 9, the generator assembly includes a housing 102 formed of plastic, e.g. nylon, or any other suitable material or combination of materials. A central cavity 104 is formed in one end of the housing for receiving a drive assembly 42, and a cap 106 is provided for securing the drive assembly in the housing. Suitable fasteners are provided for securing the end cap to the housing.

The construction of the drive assembly 42 is substantially identical to that described above with reference to FIG. 1, and the various components of the assembly are provided with the same numerals in the figures. The wires 24 from the stator coils 48 extend from the assembly 42 through a passage to the coupling 100 of the power cord so that current from the generator 44 is delivered to the lamp.

The housing 102 includes an inlet passage 108 extending between a male coupling and the pneumatic motor 46, and an outlet passage 110 leading from the pneumatic motor. A valve 112 is provided in the inlet passage for controlling the flow of compressed air to the motor. The valve 112 is a conventional regulator valve capable of controlling the amount of compressed air delivered to the motor 46. The nozzle 72 opening up to the vanes 54 of the motor 46 from the inlet passage is preferably angled so that compressed air entering the motor drives the shaft 50.

The outlet nozzle 74 permits communication between the motor 46 and the outlet passage 110, and a female coupling is provided for delivering exhausted compressed air from the drive assembly 42 to the tool 82 via the conduit or line 86. A check valve 114 is positioned in an exhaust line between the nozzle 74 and the conduit or line 86, and permits air to be exhausted from the apparatus when the tool is not in use. Thus, it is possible to generate electricity for the lighting apparatus even when the tool is not being used.

The lighting apparatus and tool illustrated in FIG. 10 are substantially similar to the apparatus shown in FIGS. 8 and 9, and common elements are provided with common reference numerals in order to assist in the description of this construction.

The lighting apparatus illustrated in FIG. 10 includes a generator housing 116, an optic fiber 118 having first and second ends, a connection means for connecting the first end of the optic fiber to the housing, and a mounting means for mounting the second end of the optic fiber on the tool to direct focused light onto the immediate area surrounding the point at which work is being done.

The mounting means includes a removable strap 98 which fits around the tool, and a clip 120 secured to the strap for holding the optic fiber in position. The connection means includes a threaded coupling 122 secured to the first end of the optic fiber. The coupling orients the optic fiber relative to a lamp 124 within the generator housing 116, shown in FIG. 11, so that light emitted by the lamp is transmitted through the fiber and is directed onto the work area.

The generator housing includes an inlet passage 108, an outlet passage 110 and an exhaust 126. A conduit 128 is connected between the outlet passage and an inlet of the tool 82. Preferably, the conduit is a short, rigid element which provides mechanical support of the housing beneath the handle of the tool in addition to providing for the passage of compressed air between the housing and the tool.

The generator housing includes a central cavity 104 within which the drive assembly 42 is received. The cavity is closed off at its open end by a cover plate 130 which includes a lamp assembly 132. The lamp assembly includes the lamp 124 supported in a socket, a reflector 134 for directing light emitted from the lamp directly into the first end of the optic fiber, and a threaded sleeve 136 on which the coupling of the connection means is received. Wires 24 extend between the coils 48 of the generator 44 and the socket in order to provide electricity to the lamp during operation of the generator.

As shown in FIG. 12, a reflector 138 is provided that is adapted to be received on the threaded sleeve 136 of the lamp assembly 132 in place of the coupling 122. The reflector 138 includes a threaded connector 140 for fastening the reflector to the sleeve 136, and a central, angled opening through which light passes. The surface 142 of the opening is coated with a reflective material so that light emitted by the lamp is directed onto the general area surrounding the point at which the tool is directed. The reflector may be used in place of the optic fiber in order to provide illumination of a work area.

A tool apparatus is illustrated in FIG. 13, and includes a tool body 144 having an inlet 146 adapted for connection to a source of compressed air, and an exhaust 148 for exhausting compressed air from the tool. A pneumatic motor 150 is provided within the body and is connected between the inlet and the exhaust. An output shaft 152 is supported on the body and driven by the pneumatic motor 150 through a suitable gear reduction means.

The body 144 also includes a handle within which a cavity is formed for receiving the drive assembly 42. The drive assembly is retained within the handle by a cover plate which closes off the cavity and secures the generator assembly in place.

The inlet 146 of the tool is in communication with a supply passage 154 leading to the pneumatic motor 150. A branch passage 156 communicates with the supply passage and a manually operable control valve 158 is provided on the handle for controlling the flow of compressed air through both the supply passage and the branch passage. An inlet passage 160 also communicates with the control valve 158 and extends between the valve and the pneumatic motor 46 of the drive assembly 42. The pneumatic motor communicates with an outlet passage 162 which leads to an exhaust. Preferably, a check valve or manual regulator valve 164 is provided in the exhaust for controlling the flow of compressed air through the pneumatic motor.

The shaft 152 extends through a forward end of the tool body and, in the construction shown, terminates at a chuck 166 adapted to receive various rotatable tool bits. It is noted that although a rotary tool is illustrated, the tool may alternately employ an oscillating shaft or any other type of known mechanical output. At least one lamp 168 is supported at the forward end of the body and is received within a socket which connects the electrical contacts of the lamp with the wires 24 extending from the 48 coils of the generator 44. A reflector 170 may also be provided in association with each lamp for directing light forward of the tool onto the work being done. Further, a clear lens 172 may be fitted over the lamps and the forward end of the body in order to protect the lamps from breakage.

The control valve 158 is affixed to a manually operable trigger on the handle of the tool and is normally biased by a spring 174 toward a closed position in which an opening 174 formed in the valve is removed from communication with both the supply passage 154 and the branch passage 156, as shown in FIG. 13. When the trigger is partially depressed, as shown in FIG. 14, the opening 176 communicates with the branch passage 156 and the inlet passage 160 to permit compressed air to flow to the drive assembly 42 so that electricity is generated and the lamps energized. However, because the supply passage 154 remains closed, the tool remains inactivated.

Upon complete depression of the trigger, as shown in FIG. 15, the branch passage 156 and inlet passage 160 remain in communication with one another, and the supply passage 154 is opened, allowing compressed air to flow to the pneumatic motor 150 of the tool. In this position of the valve 158, both the lamp and the tool are driven by the compressed air supplied to the tool.

If it is desired to operate the tool without the lamp being energized, the control valve at the exhaust of the pneumatic motor is closed, shutting down the pneumatic motor.

It is noted that the illustration of this construction, and of all of the described constructions of the preferred embodiment are schematic, and that the elements actually used may take on any form necessary to accomplish the functions set forth in this disclosure and necessary for successful operation of the apparatus.

Another construction of the tool of FIG. 13 is illustrated in FIG. 16, and includes a battery 178 within the circuit between the lamp 168 and the drive assembly 42. The battery 178, which preferably is a DC battery, supplies electricity to the lamp regardless of the status of the generator 44 and supplies a constant current to the lamp. A transformer 180 is also included in the circuit between the drive assembly 42 and the battery 178, and serves to convert AC current generated by the assembly into DC current which is stored in the battery. Thus, the drive assembly 42 serves as a recharger for the battery in order to extend the life of the battery in use. Although not shown in the figure, a switch is provided in the circuit between the battery and the lamp for disconnecting the lamp when not in use.

Although the invention has been described with reference to the various constructions of the preferred embodiment illustrated in the attached drawing figures, it is noted that substitutions may be made and equivalents employed herein without departing from the scope of the invention as recited in the claims. For example, any one of the various drive assembly constructions described herein may be used in place of one another in any of the various illustrated constructions.

Further, although each of the constructions are illustrated as being upstream of the tool relative to the source of compressed air, it is noted that the generator assembly of any of the described constructions could be connected to the exhaust of a pneumatic tool such that the generator assembly would be downstream of the tool relative to the source of compressed air.

Finally, although certain features of the preferred embodiment have been described and illustrated with reference to only one of the constructions disclosed, it is understood that all of the features are interchangeable and are not restricted by the description given.

What is claimed is:

1. A pneumatic lighting apparatus comprising:
   a lamp;
   an electrical generator for generating electrical current in response to a mechanical input;
   an electrical circuit connecting the generator with the lamp for energizing the lamp when current is available from the generator;
   a pneumatic motor for providing the mechanical input to the generator;
   a valve means for selectively directing compressed air through the motor to drive the motor; and
   a ventilation manifold for exhausting compressed air from the apparatus after the compressed air has passed through the pneumatic motor, the ventilation manifold including a plurality of holes for directing the air exhausted from the apparatus, and being movable relative to the lamp so that the direction in which the air is exhausted may be changed.

2. A pneumatic lighting apparatus as recited in claim 1, wherein the pneumatic motor includes a turbine provided with an axial shaft and a plurality of turbine blades extending radially outward from the shaft, the apparatus further comprising drive means for directing compressed air across the blades to carry out rotary drive of the axial shaft.

3. A pneumatic lighting apparatus as recited in claim 1, wherein the electrical generator includes at least one stator coil and a rotor shaft movable relative to the coil and provided with a permanent magnet for generating a current in the coil during rotation of the rotor shaft.

4. A pneumatic lighting apparatus as recited in claim 1, wherein the pneumatic motor includes a turbine provided with an axial shaft and a plurality of turbine blades radially outward from the shaft, and the electrical generator includes at least one stator coil and a rotor shaft that is rotatable relative to the coil, the axial shaft of the motor and the rotor shaft of the electrical generator being collinear.

5. A pneumatic lighting apparatus as recited in claim 4, wherein the axial shaft of the motor and the rotor shaft are unitary.

6. A pneumatic lighting apparatus for use with a pneumatically driven tool provided with an air inlet, the apparatus comprising:
   a lamp for emitting light adapted to be directed onto an area in which the tool is being used;
   generator housing including an inlet adapted for connection to a source of compressed air, an outlet, and an exhaust;
   a conduit for connecting the outlet of the housing with the air inlet of the tool to deliver compressed air from the apparatus to the tool;
   a pneumatic motor in the housing connected between the inlet and the outlet, the motor being driven by compressed air passing through the apparatus and providing a mechanical output;
   an electrical generator that is driven by the mechanical output of the motor for generating electrical current;
   an electrical circuit including the generator and the lamp for supplying electricity to the lamp;
   a control valve means for controlling the flow of compressed air through the motor; and
   an exhaust valve means for controlling the flow of compressed air from the exhaust, the exhaust valve means permitting compressed air to flow from the exhaust when the tool is not in use so that the lighting apparatus may be used independent of the tool.

7. A pneumatic lighting apparatus as recited in claim 6, wherein the pneumatic motor includes a turbine provided with an axial shaft and a plurality of turbine blades extending radially outward from the shaft, the apparatus further comprising drive means for directing compressed air across the blades to carry out rotary drive of the axial shaft.

8. A pneumatic lighting apparatus as recited in claim 6, wherein the electrical generator includes at least one stator coil that is fixed relative to the generator housing, and a rotor shaft movable relative to the coil and provided with a permanent magnet for generating a current in the coil during rotation of the rotor shaft.

9. A pneumatic lighting apparatus as recited in claim 1, wherein the pneumatic motor includes a turbine provided with an axial shaft and a plurality of turbine blades extending radially outward from the shaft, and the electrical generator includes at least one stator coil that is fixed relative to the generator housing and a rotor shaft that is rotatable relative to the coil, the axial shaft of the motor and the rotor shaft of the electrical generator being collinear.

10. A pneumatic lighting apparatus as recited in claim 9, wherein the axial shaft of the motor and the rotor shaft are unitary.

11. A pneumatic lighting apparatus as recited in claim 6, wherein the conduit is rigid and is adapted to provide mechanical support of the apparatus on the tool.

12. A pneumatic lighting apparatus as recited in claim 6, further comprising carrying means for permitting the apparatus to be carried by a user.

13. A pneumatic lighting apparatus as recited in claim 6, further comprising mounting means for mounting the apparatus on the tool and for permitting removal of the apparatus from the tool.

14. A pneumatic lighting apparatus as recited in claim 6, further comprising means for mounting the lamp on the tool and for directing light emitted by the light onto the area in which the tool is being used.

15. A pneumatic lighting apparatus as recited in claim 6, wherein the lamp is supported on the generator housing, the apparatus further comprising an elongated optic fiber having first and second ends, a connection means for connecting the first end of the optic fiber to the housing and coupling the fiber with the lamp so that light emitted by the lamp is transmitted through the optic fiber and a mounting means for mounting the second end of the optic fiber on the tool so that the light transmitted through the fiber may be directed onto the area in which the tool is being used.

16. A pneumatic lighting apparatus as recited in claim 6, wherein the mounting means includes a removable clip which allows attachment and detachment of the second end of the optic fiber on the tool.

17. A pneumatic lighting apparatus as recited in claim 14, wherein the mounting means includes a removable clip which allows attachment and detachment of the lamp on the tool.

18. A pneumatic lighting apparatus as recited in claim 6, wherein the circuit includes a transformer for converting the current generated by the electrical generator into direct current, and a battery for storing the direct current.

19. A pneumatic lighting apparatus as recited in claim 6, wherein the exhaust valve means includes a check valve that automatically releases compressed air from the housing when the pressure of the air exceeds a predetermined value.

20. A pneumatic tool comprising:
a housing including an inlet adapted for connection to a source of compressed air, and an exhaust means for exhausting compressed air from the housing;
a first pneumatic motor in the housing connected between the inlet and the exhaust means, and being driven by compressed air;
an output shaft supported on the housing and driven by the first pneumatic motor;
a second pneumatic motor in the housing connected between the inlet and the exhaust means, and being driven by compressed air to provide a mechanical output;
an electrical generator that is driven by the mechanical output of the motor for generating electrical current;
a lamp supported on the housing;
an electrical circuit connecting the generator and the lamp for supplying electricity to the lamp; and
a control valve means for controlling the flow of compressed air through the first and second motors.

21. A pneumatic tool as recited in claim 20, wherein the second pneumatic motor includes a turbine provided with an axial shaft and a plurality of turbine blades extending radially outward from the shaft, the apparatus further comprising drive means for directing compressed air across the blades to carry out rotary drive of the axial shaft.

22. A pneumatic tool as recited in claim 20, wherein the electrical generator includes at least one stator coil that is fixed relative to the housing, and a rotor shaft movable relative to the coil and provided with a permanent magnet for generating a current in the coil during rotation of the rotor shaft.

23. A pneumatic tool as recited in claim 20, wherein the second pneumatic motor includes a turbine provided with an axial shaft and a plurality of turbine blades extending radially outward from the shaft, and the electrical generator includes at least one stator coil that is fixed relative to the housing and a rotor shaft that is rotatable relative to the coil, the axial shaft of the motor and the rotor shaft of the electrical generator being collinear.

24. A pneumatic tool as recited in claim 23, wherein the axial shaft of the second motor and the rotor shaft are unitary.

25. A pneumatic tool as recited in claim 20, wherein the circuit includes a transformer for converting the current generated by the electrical generator into direct current, and a battery for storing the direct current.

26. A pneumatic tool as recited in claim 20, wherein the exhaust means includes a check valve that automatically releases compressed air from the housing when the pressure of the air exceeds a predetermined value.

* * * * *